United States Patent [19]
Emery et al.

[11] Patent Number: 4,657,930
[45] Date of Patent: Apr. 14, 1987

[54] MITOTIC INHIBITORS PREVENTING POSTERIOR LENS CAPSULE OPACIFICATION

[75] Inventors: Jared M. Emery, Houston, Tex.; Raymond Y. Chan, San Diego, Calif.

[73] Assignee: Baylor College of Medicine, Houston, Tex.

[21] Appl. No.: 708,753

[22] Filed: Mar. 6, 1985

Related U.S. Application Data

[60] Division of Ser. No. 516,166, Jul. 20, 1983, Pat. No. 4,515,794, and a continuation-in-part of Ser. No. 310,159, Oct. 9, 1981, abandoned.

[51] Int. Cl.⁴ .............................................. A61K 31/19
[52] U.S. Cl. .................................... 514/557; 514/912
[58] Field of Search ................................ 514/557, 912

[56] References Cited

U.S. PATENT DOCUMENTS 3,089,823  5/1963  Czarnecki ........................ 424/81

FOREIGN PATENT DOCUMENTS 1431841  4/1976  United Kingdom .

OTHER PUBLICATIONS

Dispersa—Therapeutic Index—re: Vitamin A.
ARVO-1984-Invest. Ophth. & Vis. Sci. 25 (3)(1984)—Ubels et al.—Vitamin A is Present as Retinol in Tears.
Chem. Abst. 99:47928t (1983)—Chan et al.
Chem. Abst. 99:47929n (1983)—Baylor College of Med.

*Primary Examiner*—Douglas W. Robinson
*Attorney, Agent, or Firm*—Fulbright & Jaworski

[57] ABSTRACT

Disclosed are mitotic inhibitors effective for and methods of preventing posterior lens capsule opacification after extracapsular extraction. The mitotic inhibitors comprise osmotically balanced solutions containing either methotrexate or retinoic acid, or both, in at least the minimal effective dosage at the end of one lens epithelial cell cycle. The mitotic inhibitors are instilled in the anterior chamber of the eye preferably immediately after the lens has been removed.

3 Claims, No Drawings

MITOTIC INHIBITORS PREVENTING POSTERIOR LENS CAPSULE OPACIFICATION

REFERENCE TO RELATED APPLICATION

The present application is a division of application Ser. No. 516,166, filed July 20, 1983, now U.S. Pat. No. 4,515,794 and a continuation-in-part of application Ser. No. 06/310,159 filed Oct. 9, 1981, abandoned in favor of the continuation-in-part application.

BACKGROUND OF THE INVENTION

Extracapsular cataract extraction has recently become a more popular method of removing cataracts, probably because of its lower incidence of post-operative complications in terms of cystoid macular edema and possible retinal detachment. The advent of an improved extracapsular extraction technique such as phacoemulsification and the requirement of an intact posterior lens capsule for implantation of a wide variety of intraocular lenses have certainly played an important role in influencing such a trend. The only possible disadvantage of extracapsular cataract extraction is the high incidence of posterior lens capsule opacification, which requires additional surgical procedures (posterior capsulotomy or repolishing of the posterior lens capsule) to obtain good vision.

The pathogenesis of posterior lens capsule opacification after extracapsular cataract extraction is known: the remnant lens epithelial cells proliferate on the posterior lens capsule to form abortive lens "fibers" and "bladder" cells (i.e. Elschnig's pearls).

As reported in Contact and Intraocular Lens Medical Journal, Vol. 5, No. 4, Oct./Dec. 1979, pp. 175–178, After-Cataract: Studies of Chemical and Radiation Inhibition, by Roy et al, chemical and radiation means have been attempted to try to find a method associated with extracapsular cataract surgery which would lower the incident of after cataract growth. As reported in this publication the chemicals used (vincristine and vinblastine) were tried to chemically inhibit subcapsular epithelial cells because they had been found to have a direct inhibitory effect on cell mitosis (Goodman, L. S., and Gillman, A: The Pharmacological Basis of therapeutics, Maximilan, New York, 1965, pp. 1373–1376). Vincristine and vinblastine were found to inhibit the corneal wound so that it healed poorly, and because of the deletory effects to the cornea and iris it was the opinion of the authors that these drugs should not be used in further animal studies to try to inhibit subcapsular epithelial perforation. The authors further stated that radiation given the second day after surgery appeared to be the most effective of all dosage schedules, however, they indicate that there is some danger of injury, the authors concluding that it is difficult to say, however, that if one used radiation in humans whether there would be problems or not.

The authors further pointed out that if there were a drug or chemical system that could be found which would inhibit selectively the subcapsular epithelial cells, this might be a useful way to help prevent after cataracts.

PRIOR ART STATEMENT

Methotrexate is an antimetabolic which inhibits the enzyme, dihydrofolate reductase, and blocks cell division at metaphase. Because of this property of methotrexate when it is applied intravenously (i.v.) to a cancer patient, it kills all dividing cells in the body, hopefully a higher percentage of the cancer cells because the tumor cells have higher rates and divide in a more synchronous fashion. However, during i.v. administration of methotrexate, fast dividing normal human cells are also affected. i.e., the bone marrow, white blood cells, epithelial cells of the gastrointestinal tract, hair cells, and a minimal percentage of epithelial cells.

Bisantes, et al, Chem. Abst. 583t, 1975 report the fall in mitotic rate of rabbit lens epithelium after intraperitoneal (i.p.) administration of methotrexate in a dosage calculated on milligrams of methotrexate per kilogram of weight, as reported in all studies to applicants' knowledge.

Retinoic acid is synthetic analogs of vitamin A. Current studies show that it prevents the development of Squamous Metaplasia and carcinoma in the bladder, mammary gland and respiratory tract of animals exposed to chemical carcinogens.

Retinoic Acid (retinyl methylether or retinyl acetate) is used clinically for treatment of cystic acne in oral or topical form. The exact mechanism of retinoic acid is not known. It appears to inhibit cellular division or the synthesis of DNA or both.

While methotrexate and retinoic acid have been available for decades, applicants are unaware of any use or publication which discloses or suggests the instilling of methotrexate or retinoic acid in the anterior chamber of the eye after extracapsular extraction to prevent posterior lens capsule opacification without ocular compromise. Also, the instillation into the anterior chamber of the eye of an osmotically bqalanced solution of methatrexate, retinoic acid or mixtures thereof in concentrations of at least the minimal effective dosage at the end of one lens epithelial cell cycle to effectively inhibit subcapsular epithelial cell growth has not been used or suggested for use in any prior art publication.

SUMMARY OF THE INVENTION

The present invention is directed to mitotic inhibitors effective to inhibit and to methods of selectively inhibiting subcapsular epithelial growth by instilling mitotic inhibitors, that is, osmotically balanced solutions of methotrexate or retinoic acid, or mixtures thereof, into the anterior chamber of the eye immediately following cataract surgery in initial concentrations to provide a minimal effective dosage of each agent. This is accomplished by realizing the minimal effective dosage of each agent, the lens epithelial cell-cycle time, the rate of aqueous humor formation and exit, and the volume of the anterior segment compartments after lens extraction. The initial concentration can then be calculated as set forth in the subsequent description of preferred embodiments. Colchicine, in such minimal effective dosage, prevents posterior lens capsule opacification, but with some optic nerve toxicity.

Accordingly, it is an object of the present invention to provide mitotic inhibitors which when instilled into the anterior chamber of the eye following lens removal effectively inhibits subcapsular epithelial growth.

It is a further object of the present invention to provide an osmotically balanced solution of either methotrexate or retinoic acid, or mixtures thereof, in concentrations to provide a minimal effective dosage when instilled into the anterior chamber of the eye after lens removal thereby effectively inhibiting subcapsular epithelial growth.

It is an object of the present invention to provide a method of selectively inhibiting the subcapsular epithelial cells to help prevent after-cataracts.

It is a further object of the present invention to provide a method of preventing future proliferation of the remnant lens epithelial cells, hence preventing the opacification of the posterior lens by instilling osmotically balanced solutions of methotrexate or retinoic acid, or mixtures thereof, into the anterior chamber of the eye after extracapsular cataract extraction.

A further object of the present invention is the provision of a method in which the mitotic inhibitor is concentrated in the anterior segment compartments of the eye above the minimal effective dosage at the end of one lens epithelial cell cycle.

Other and further objects, features and advantages appear throughout the specification and claims.

DESCRIPTION OF PREFERRED EMBODIMENTS

Mitotic inhibitors, osmotically balanced solutions of methotrexate or retinoic acid at precalculated dosages, are instilled into the anterior chamber of the eye, preferably immediately after extracapsular cataract extraction which effectively prevent future proliferation of remnant lens epithelial cells, hence preventing the opacification of the posterior lens capsule.

Methotrexate is a cycle-dependant antimetabolite, it inhibits the enzyme dihydrofolate reductase and thus interferes with the maintenance of intracellular pools of reduced folates.

Retinoic Acid, the exact mechanism is unknown, appears to inhibit either cellular division or DNA synthesis (or both).

Colchicine arrests mitosis at metaphase by binding to a protein present in microtubules, hence interfering with the structure of the mitotic spindle.

Methotrexate, retinoic acid and colchicine are all known chemical compounds, are readily available, and no detailed description thereof is given or deemed necessary.

Since all of the structures in contact with the anterior and posterior chambers (corneal endothelium, ciliary epithelium, iris pigment epithelium, muscle, and neural elements) are postmitotic, cycle-dependent mitotic inhibitors theoretically should affect only the actively dividing lens epithelial cells.

It is essential to determine the necessary initial concentration of each mitotic inhibitor in the anterior segment compartments. This can be accomplished by realizing the minimal effective dosage of each agent, the lens epithelial cell-cycle time, the rate of aqueous humor formation and exit, and the volume of the anterior segment compartments after lens extraction. The initial concentration can then be calculated from an approximated first-order linear differential equation describing the aqueous humor dynamics:

v = volume of anterior segment compartments
r = rate of aqueous formation (assumed to be equal to aqueous exit in steady state)
C = concentration of the drug
Co = initial concentration
Ct = concentration at time t
Then $$C_t = C_o e^{-0.00357\, t} = C_o e^{-4.284} \text{ (assuming } t=1,200 \text{ minutes)}$$

For Methotrexate:

$$C_t = 10^{-6}M = C_o e^{-4.284}$$

$$\therefore C_o = (10^{-6}M)(e^{4.284}) \approx 10^{-4}M = 0.0454 \text{ mg/cc}$$

Retinoic acid:

$$C_t = 10^{-6}M = C_o e^{-4.284}$$

$$\therefore C_o = (10^{-6}M)(e^{4.284}) \approx 10^{-4}M = 0.033 \text{ mg/cc}$$

Colchicine:

$$C_t = 10^{-6}M = C_o e^{-4.284}$$

$$\therefore C_o = (10^{-6}M)(e^{4.284}) \rightarrow 72.5 \times 10^{-6}M = 0.04 \text{ mg/cc}$$

The carrier or solution can be a variety of solutions. It essentially is a sterile osmotically balanced solution, many of which are available on the market; for example, the following:

BSS (Balanced Salt Solution) is a sterile balanced salt solution isotonic to tissues of the eye. Each ml contains sodium chloride 0.64%, potassium chloride 0.075%, calcium chloride 0.048%, magnesium chloride 0.030%, sodium acetate 0.39%, sodium citrate 0.17%, sodium hydroxide and/or hydrochloric acid (to adjust pH) and water for injection.

Miostat is a sterile balanced salt solution of carbachol for intraocular injection. The active ingredient is represented by the chemical structure:

[NH₂COOCH₂CH₂N+(CH₃)₃]Cl

Zolyse is a lyophilized form of crystalline alpha-chymotrypsin, a proteolytic enzyme obtained from the pancreas of the ox. The diluent is a sterile balanced salt solution. One 9 ml vial of diluent contains: sodium chloride 0.49%, sodium acetate 0.39%, sodium citrate 0.17%, potassium chloride 0.075%, calcium chloride 0.048%, magnesium chloride 0.03%, hydrochloric acid and/or sodium hydroxide (to adjust pH) and water for injection.

Catarase is a 1:5,000 dilution of chymotrypsin in an isotonic, sodium chloride solution.

The diluents used are either BSS for Miostat and Zolyse or sterile sodium chloride solution for Catarase.

Further information and details are set forth in the Physicians' Desk Reference.

Preferably, the mitotic inhibitor is instilled by drops into the anterior chamber of the eye immediately following lens removal when the wound is still open from the lens removal.

EXAMPLE 1

In this example, extracapsular lens extraction by phacoemulsification was performed in both eyes of three older primates (*Macaca fascicularis*) and three pigmented rabbits (*Oryctolagus cuniculus*). Osmotically balanced solutions of methotrexate, retinoic acid, and colchicine were instilled above each of their minimal effective dose into the anterior chamber of one eye of each of the primates and pigmented rabbits immediately following cataract surgery, with the other eye of the same primate and rabbit serving as an operated control.

To determine the effects of the mitotic inhibitors on the remnant epithelial cells, the rabbits were sacrificed six weeks postoperatively despite the lack of any opacifications along the posterior capsules in either the control (operated) or experimental (operated plus mitotic inhibitor instillation). The isolated posterior capsules of the control and experimental animals were processed for electron microscopy and infiltrated in Epon-Araldite. Characteristic light and electron micrographs were taken.

Consistently with all three mitotic inhibitors, light microscopy revealed a homogeneous population of spindle-shaped cells in the angles between the collapsed thick anterior and thin posterior capsules. Uniformly, with all three mitotic inhibitors, any remnant lens epithelial cells along the anterior capsule were non-mitotic, non-pycnotic, and contained contorted interphase nuclei, atrophic mitochondria, and bloated, irregular rough endoplasmic reticulum. With all three mitotic inhibitors, the spindle cells ultrastructurally were not lens fibers but were transformed arrested lens epithelium that was induced by the mitotic inhibitors to become elongated cells with non-pycnotic nuclei, atrophic mitochondria, and irregular rough endoplasmic reticulum.

Each primate and rabbit was followed with slit-lamp photographs of the posterior lens capsule, endothelial cell counts, and corneal thickness measurements preoperatively, then again at 6 weeks, 4 months, and 8 months postoperatively. Electroretinograms (ERGs) and visual evoked responses (VERs) were recorded preoperatively and then at 6 weeks, 4 months, and 8 months postoperatively.

The most striking clinical result was in the eyes instilled with methotrexate. There was a crystal-clear posterior lens capsule in the experimental eyes; whereas the posterior lens capsule in the control eyes had been completely opacified by the proliferating lens epithelial cells with early developing Elschnig's pearls.

In the eyes instilled with retinoic acid there was a clear central posterior lens capsule with tiny islands of proliferating lens epithelial cells in the far periphery. In the contralateral control eyes there were also a clear central posterior capsule. However, extensive islands of lens epithelial cell proliferation occurred in the midperiphery.

The posterior lens capsules in the colchicine-injected eyes were clear centrally with peripheral lens epithelial island; however, the control eye showed large islands of epithelial cells with a suggestion of cells breaking through to the posterior clear capsule.

From the sequential ERGs, VERs, endothelial cell counts, and corneal thickness measurements, no ocular toxicity was found in the eyes instilled with methotrexate or retinoic acid, but apparent ent optic nerve toxicity was seen in the eyes instilled with colchicine.

EXAMPLE 2

In this example, extracapsular lens extraction by phacoemulsification was performed in both eyes of four younger primates (approximate human equivalent of 7-10 years old). A solution of methotrexate was instilled in one eye of each of the primates as in Example 1. At two months post-operation, 2 of the 4 posterior lens capsules from the controlled eyes had opacified while all 4 posterior lens capsules instilled with methotrexate remained clear.

From the foregoing examples, and the data obtained, osmotically balanced solutions of methotrexate and retinoic acid are safe agents to use to prevent posterior lens capsule opacification, with no apparent ocular toxicity or adverse side effects. Colchicine does prevent posterior lens capsule opacification, but apparently there is some optic nerve toxicity associated with its use.

The instillation of osmotically balanced solutions of methotrexate and retinoic acid in the precalculated dosage as set forth above, is effective to prevent posterior lens capsule opacification without ocular compromise after extracapsular cataract extraction, while instillation of osmotically balanced solutions of colchicine prevents posterior lens capsule opacification but with some optic nerve toxicity. The use of these mitotic inhibitors minimizes opacification of an intact posterior lens capsule postoperatively, and thereby greatly reduces the complications of cataract surgery, such as cystoid macular edema, retinal detachment, and the corneovitreous touch syndrome.

The present invention, therefore, is well suited and adapted to attain the objects and ends and has the advantages and features mentioned as well as others inherent therein.

While presently preferred embodiments have been given for the purpose of disclosure, changes can be made therein which are within the spirit of the invention as defined by the scope of the appended claims.

What is claimed is:

1. A mitotic inhibitor effective to prevent proliferation of remnant lens epithelial cells when intraocularly instilled into the anterior chamber of the eye after extracapsular extraction comprising,
   an osmotically balanced solution containing a minimum concentration of 0.033 mg of retinoic acid per cc of solution.

2. A method of preventing proliferation of remnant lens epithelial cells after extracapsular cataract extraction comprising,
   intraocularly instilling into the anterior chamber of the eye after the extracapsular extraction a mitotic inhibitor comprising an osmotically balanced solution containing a minimum concentration of 0.033 mg of retinoic acid per cc of solution.

3. A method of preventing proliferation of remnant lens epithelial cells after extracapsular cataract extraction comprising,
   intraocularly instilling the mitotic inhibitor of claim 2 immediately following the cataract extraction.

* * * * *

UNITED STATES PATENT OFFICE
CERTIFICATE OF CORRECTION

Patent No. 4,657,930             Dated    April 14, 1987

Inventor(s) Raymond Y. Chan and Jared M. Emery

It is certified that error appears in the above-identified patent and that said Letters Patent are hereby corrected as shown below:

Column 2, line 6, "affected." should read --affected,--.

Column 2, line 32, "bqalanced" should read --balanced--.

Column 2, line 33, "methatrexate," should read --methotrexate,--.

Column 5, line 49, after "apparent" delete -- ent --.

Signed and Sealed this

Eighteenth Day of August, 1987

Attest:

DONALD J. QUIGG

Attesting Officer        Commissioner of Patents and Trademarks